United States Patent
Kobayashi et al.

(10) Patent No.: US 7,105,320 B2
(45) Date of Patent: Sep. 12, 2006

(54) PROCESS FOR PRODUCING HYALURONIC ACID OR ITS DERIVATIVE

(75) Inventors: Shiro Kobayashi, Kyoto (JP); Masashi Ohmae, Kyoto (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 477 days.

(21) Appl. No.: 10/469,984

(22) PCT Filed: Mar. 14, 2002

(86) PCT No.: PCT/JP02/02431

§ 371 (c)(1), (2), (4) Date: Sep. 15, 2003

(87) PCT Pub. No.: WO02/072860

PCT Pub. Date: Sep. 19, 2002

(65) Prior Publication Data

US 2004/0132142 A1 Jul. 8, 2004

(30) Foreign Application Priority Data

Mar. 14, 2001 (JP) ............................. 2001-071873

(51) Int. Cl.
*C12P 19/04* (2006.01)
*C08B 37/00* (2006.01)

(52) U.S. Cl. ........................ 435/101; 435/72; 536/123; 536/123.1; 536/126

(58) Field of Classification Search ................ 435/101, 435/72; 536/126, 123, 123.1
See application file for complete search history.

(56) References Cited

FOREIGN PATENT DOCUMENTS

JP 9-3088 1/1997

OTHER PUBLICATIONS

S. Kobayashi et al.: "Enzymatic polymerization to artificial hyaluronan: A novel method to synthesize a glycosaminoglycan using a transition state analogue monomer" J. Am. Chem. Soc., vol. 123, No. 47, pp. 11825-11826 Nov. 28, 2001.

Shiro Kobayashi et al.: "GlcA-beta (1-3)-GlcNAc oxazoline yudotai o shinki kishitsu monomer to shita koso shokubai jugo ni yoru hyaluronic acid no gosei" Chemical Society of Japan Koen Yokoshu, vol. 79, No. 2, p. 815 Mar. 15, 2001.
Shiro Kobayashi et al.: "Hiarobiuroneto oxazoline yudotai o sen'i jotai analogue kisitsu to shita koso shokubai jugo ni yoru jinko hyaluronic acid no gosei" Polymer Preprints, Japan, vol. 50, No. 14, p. 3517 Aug. 28, 2001.
Shiro Kobayashi et al.: "Koso shokubai jugo ni yoru jinko hyaluronic acid no gosei" Polymer Preprints, Japan, vol. 50, No. 5, p. 997 May 7, 2002.
Shiro Kobayashi et al.: "Hyaluronidase koso shokubai jugo ni yoru jinko hyaluronic acid no gosei" Nihon Toshitsu Gakkai Nenkai Yoshishu, p. 146 Jul. 2, 2001.
S. Kobayashi et al.: "Enzymatic ring-opening polyaddition for chitin synthesis: a cationic mechanism in basic solution?" Macromol. Symp., vol. 132, pp. 415-420 1998.
S. Kobayashi et al.: "Synthesis of artificial chitin: irreversible catalytic behavior of a glycosyl hydrolase through a transition state analogue substrate" J. Am. Chem. Soc., vol. 118, pp. 13113-13114 1996.
D.L. Claudio et al.: "Enzymatic synthesis of hyaluronic acid with regeneration of sugar nucleotides" J. Am. Chem. Soc., vol. 117, pp. 5869-5870 1995.
S. Kobayashi et al.: "Novel method for polysaccharide synthesis using an enzyme: the first in vitro synthesis of cellulose via a nonbiosynthetic path utilizing cellulose as catalyst" J. Am. Chem. Soc., vol. 113, pp. 3079-3084 1991.
R.W. Jeanloz et al.: The synthesis of P-[2-acetamido=2-deoxy-3-0(Beta-D-glucopyranosyluronic acid)-alpha-D-glucopyranosyl]P-dolichyl diphosphate (N-acetyl hyalobio syluronic dolichyl diphosphate) Carbohydrate Research, vol. 68, pp. 343-363 1979.
Hiromi Saitoh et al.: "Enzymic reconstruction of glycosaminoglycan oligosaccharide chains using the transglycosylation reaction of ovine testicular hyaluronidase" The Journal of Biological Chemistry, vol. 270, No. 8, pp. 3741-3747 1995.

*Primary Examiner*—Francisco Prats
(74) *Attorney, Agent, or Firm*—Oblon, Spivak, McClelland, Maier & Neustadt, P.C.

(57) ABSTRACT

It is to provide a method for producing hyaluronic acid or a hyaluronic acid derivative which is a simple preparation method as compared with a cockscomb extraction method or a fermentation method which has conventionally been employed industrially, and with which isolation and purification of the product from the reaction liquid is easy. It is a method for producing hyaluronic acid or a hyaluronic acid derivative, which comprises acting a hyaluronidase on an oxazoline derivative.

20 Claims, 7 Drawing Sheets

● : No enzyme added
■ : Bovine testicular hyaluronidase
▲ : Ovine testicular hyaluronidase Bovine testicular hyaluronidase Ovine testicular hyaluronidase

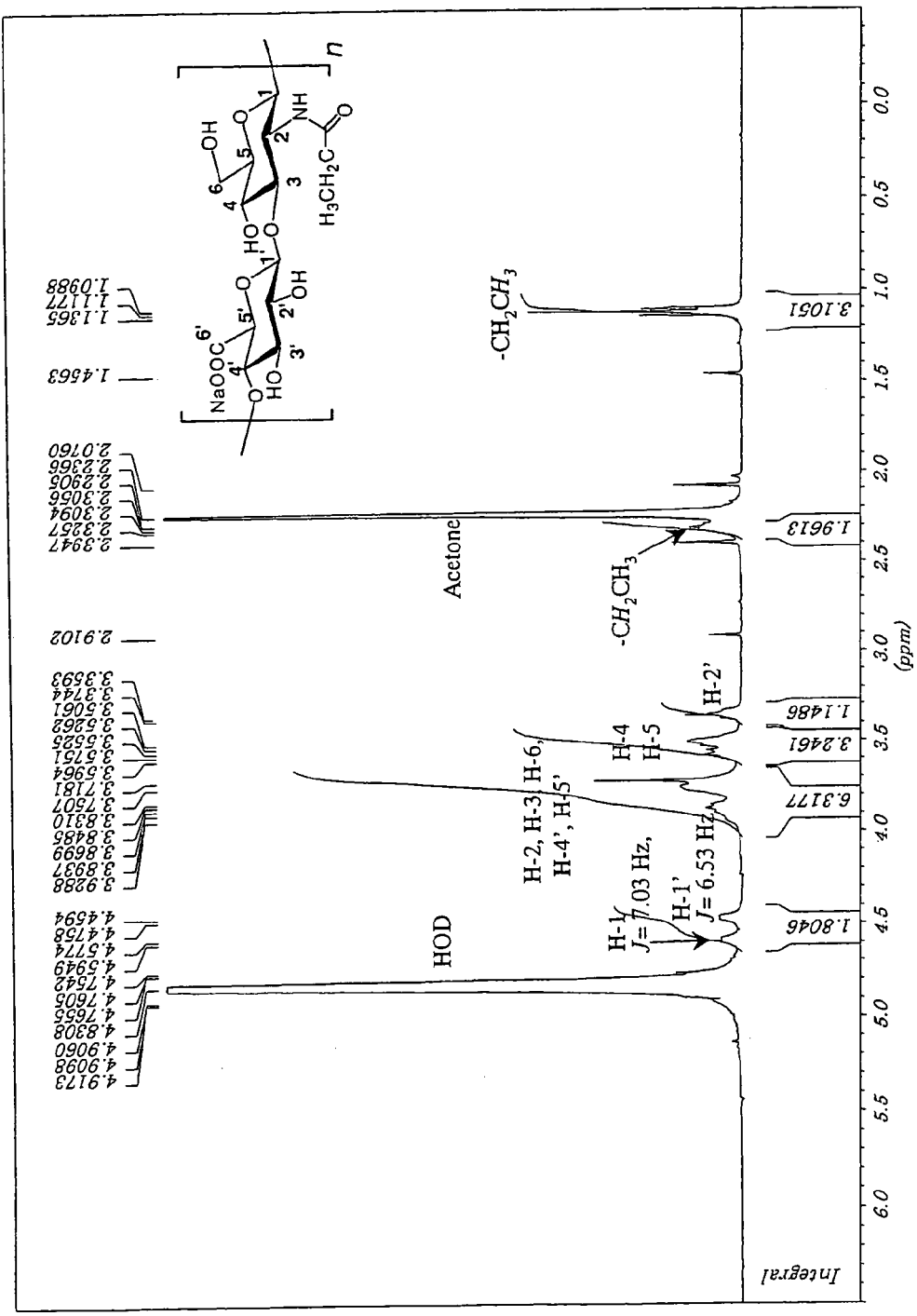
Fig. 7  $^1$H NMR spectrum of formed propanamide derivative

PROCESS FOR PRODUCING HYALURONIC ACID OR ITS DERIVATIVE

TECHNICAL FIELD

The present invention relates to an enzymatic method for producing hyaluronic acid or a hyaluronic acid derivative utilizing a hyaluronidase. More particularly, it relates to a method for producing hyaluronic acid or a hyaluronic acid derivative, which comprises enzymatically polymerizing a hyalobiuronate oxazoline derivative as a monomer substrate employing hyaluronidase from mammals as a catalyst.

BACKGROUND ART

Hyaluronic acid is a macromolecular polysaccharide without branching consisting of two kinds of monosaccharides of linearly and alternately bonded D-glucuronic acid and N-acetylglucosamine. Hyaluronic acid is present in every connective tissue of animals, and its molecular weight is considered to be from several ten thousand to several million. Hyaluronic acid is characterized by having a high moisture retention property, a high viscoelasticity and a high lubricity, and making use of such characteristics, it is blended as a humectant in cosmetics, and its availability is widely recognized in the field of medicine as e.g. an injection drug for treatment of various arthropathy or adjuncts for ophthalmic operation.

As practical methods for producing hyaluronic acid, extraction from cockscombs or umbilical cords in which hyaluronic acid is contained in a large amount, and fermentation by *Streptococci* which is one type of *Lactobacillus* have been known. Regarding enzymes which concern biosynthesis of hyaluronic acid in living organism, from research results at genetic level and enzyme level, it has been clarified that hyaluronic acid is synthesized by hyaluronan synthase from two sugar nucleotides of UDP-GlcA (uridine 5'-diphosphoglucuronic acid) and UDP-GlcNAc (uridine 5'-diphospho-N-acetylglucosamine) as precursors.

On the other hand, as an example of preparation of hyaluronic acid employing a hyaluronidase used in the present invention also, it has been reported that a pyridylaminated hyaluronic acid oligomer mixture is formed in a slight amount from a reaction system in which pyridylaminated hyaluronic acid hexasaccharide as an acceptor and hyaluronic acid having a molecular weight of 800,000 as a donor coexist, utilizing the sugar transfer activity of the hyaluronidase (The Journal of Biological Chemistry 270, 3741 (1995)). In the oligomer mixture, from pyridylaminated hyaluronic acid octasaccharide (molecular weight: about 1,600) to maximum pyridylaminated hyaluronic acid docosasaccharide (molecular weight: about 4,400) are detected even though their amounts are very small.

However, development of an enzymatic preparation means which may replace extraction from cockscombs or fermentation as a conventional method for producing hyaluronic acid has not been achieved in spite of a great number of trials.

The present inventors have conducted extensive studies on development of a novel method for producing hyaluronic acid or a hyaluronic acid derivative which is highly useful at a practical level, and as a result, unexpectedly, they have found a novel method for producing hyaluronic acid or a hyaluronic acid derivative by an enzymatic means employing a hyaluronidase for the first time.

More particularly, they have found that, in research in production of hyaluronic acid or a hyaluronic acid derivative by an enzymologic means, when a hyaluronidase which has been known as an enzyme which normally decomposes hyaluronic acid is employed as an enzyme polymerization catalyst and a hyalobiuronate oxazoline derivative is employed as a monomer substrate, the monomer substrate is enzymatically polymerized to form hyaluronic acid or a hyaluronic acid derivative having a high molecular weight with a high yield. The present invention has been accomplished on the basis of these discoveries.

DISCLOSURE OF THE INVENTION

Namely, the present invention provides (1) a method for producing hyaluronic acid or a hyaluronic acid derivative, which comprises acting a hyaluronidase on an oxazoline derivative of the following formula (I):

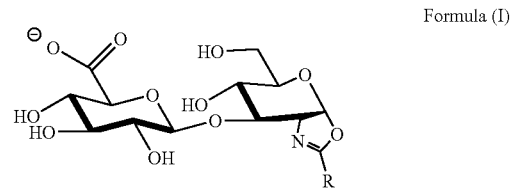

Formula (I)

wherein R is hydrogen, an alkyl group, an alkyl group which is optionally substituted, a phenyl group or a phenyl group which is optionally substituted, (2) the method for producing hyaluronic acid or a hyaluronic acid derivative according to (1), wherein the oxazoline derivative of the formula (I) is 2-methyl-[1,2-dideoxy-3-O-(sodium-D-glucopyranosyluronate)]-α-D-glucopyrano-[2,1-d]-2-oxazoline, (3) the method for producing hyaluronic acid or a hyaluronic acid derivative according to (1) or (2), wherein the hyaluronidase is hyaluronidase from mammals, (4) the method for producing hyaluronic acid or a hyaluronic acid derivative according to (3), wherein the hyaluronidase is bovine testicular hyaluronidase or ovine testicular hyaluronidase and (5) the method for producing hyaluronic acid or a hyaluronic acid derivative according to any one of (1) to (4), wherein pH is adjusted to from 5 to 10 when the hyaluronidase is acted on 2-methyl-[1,2-dideoxy-3-O-(sodium-D-glucopyranosyluronate)]-α-D-glucopyrano-[2,1-d]-2-oxazoline.

BRIEF DESCRIPTION OF THE DRAWINGS

FIG. 7 illustrates $^1$H NMR spectrum of formed propanamide derivative.

BEST MODE FOR CARRYING OUT THE INVENTION

Now, the present invention will be explained in further detail below.

Figure 1:
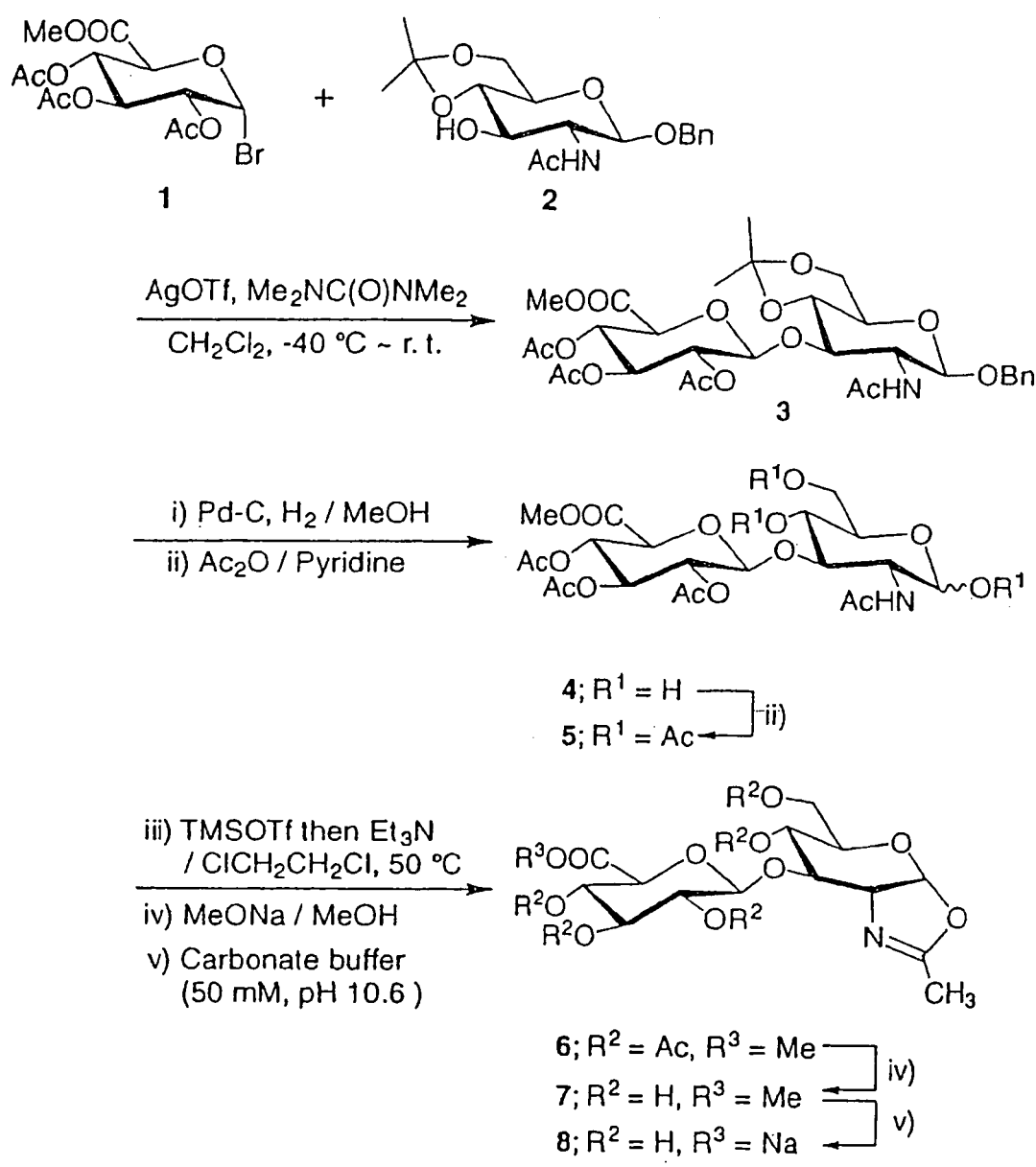
FIG. 1 is a preparation scheme.

The procedure of preparation will be shown below with reference to a hyalobiuronate oxazoline derivative (8) as one of substrate monomers employed in the present invention. Further, a preparation scheme is shown in FIG. 1.

Namely, employing methyl(2,3,4-tri-O-acetyl-α-D-glucopyranoside bromide)uronate (1) as a glycosyl donor and employing benzyl 2-acetamido-2-deoxy-4,6-O-isopropylidene-β-D-glucopyranoside (2) as a glycosyl acceptor, a reaction is started employing silver trifluoromethanesulfonate-1,1,3,3-tetramethylurea as an activating agent in dichloromethane in an atmosphere of argon at −40° C., 30 minutes later, the temperature is gradually recovered to room temperature, and a reaction is carried out at room temperature for 22 hours to prepare benzyl 2-acetamido-2-deoxy-4,6-O-isopropylidene-3-O-(methyl 2',3',4'-tri-O-acetyl-β-D-glucopyranosyluronate)-β-D-glucopyranoside (3). The obtained (3) is subjected to deblocking of the benzyl group and the isopropylidene group by means of catalytic hydrogen reduction employing 10% palladium carbon as a catalyst in dehydrated methanol in an atmosphere of hydrogen to obtain 2-acetamido-2-deoxy-3-O-(methyl 2',3',4'-tri-O-acetyl-β-D-glucopyranosyluronate)-D-glucopyranose (4). Then, acetic anhydride is acted in dehydrated pyridine to protect all hydroxyl groups with acetyl groups to obtain 2-acetamido-4,6-di-O-acetyl-2-deoxy-3-O-(methyl 2',3',4'-tri-O-acetyl-β-D-glucopyranosyluronate) -D-glucopyranosyl acetate (5). Then, trimethylsilyl trifluoromethanesulfonate is acted on (5) in 1,2-dichloroethane in an atmosphere of argon at 50° C. for 7 hours, and then triethylamine is acted thereon under cooling with ice to obtain 2-methyl[4,6-di-O-acetyl-1,2-dideoxy-3-O-(methyl 2',3',4'-tri-O-acetyl-β-D-glucopyranosyluronate) -α-D-glucopyrano-[2,1-d]-2-oxazoline (6). Sodium methoxide is acted on the obtained (6) in dehydrated methanol for deblocking of all acetyl groups, and the reaction solution is vacuum concentrated and then evaporated to dryness to obtain 2-methyl-[1,2-dideoxy-3-O-(methyl 2',3',4'-tri-O-acetyl-β-D-glucopyranosyluronate) -α-D-glucopyrano]-[2,1-d]-2-oxazoline (7).

This is stirred in a carbonic acid buffer (50 mM, pH: 10.6) for 30 minutes for deblocking of the methyl ester to obtain 2-methyl-[1,2-dideoxy-3-O-(sodium β-D -glucopyranosyluronate)]-α-D-glucopyrano-[2,1-d]-2-oxazoline (8) as an aimed substrate monomer.

The hyalobiuronate oxazoline derivative thus obtained is suitably employed as a substrate monomer for a hyaluronidase as a polymerization catalyst. The substrate monomer concentration at the time of the enzyme reaction is at least 0.1 wt % practically, preferably at least 1 wt %.

The reaction pH is from 5 to 10, preferably from 6.5 to 9.5, taking reactivity of the enzyme and stability of the substrate monomer into consideration. The reaction temperature is from 5 to 60° C., usually from 20 to 40° C.

The hyaluronidase used is preferably hyaluronidase from mammals. Specifically, bovine testicular hyaluronidase or ovine testicular hyaluronidase which is classified into endo-β-N-acetylhexosaminidase (EC3.2.1.35) is preferred, and this enzyme may be used in a form of an immobilized enzyme which is immobilized to a proper carrier. Either batch reaction or continuous reaction form may be employed.

The reaction proceeds in an aqueous solvent or under such a condition that an alcohol such as methanol, ethanol or n-propanol, a polyol such as glycerol or polyethylene glycol, dimethylsulfoxide, dimethylformamide, ethyl acetate, dioxane, or an inorganic salt or a pH buffering agent which does not impair the reaction is optionally added to an aqueous solvent.

The substrate monomer is not limited to the 2-methyhyalobiuronate oxazoline derivative (8), and substrate monomers having the hyalobiuronate oxazoline basic structure with which a polymerization reaction by a hyaluronidase proceeds are included in the present invention.

For example, in the above formula (I), R may be an alkyl group such as methyl, propyl or butyl, or a phenyl group, an alkyl group substituted with halogen or a phenyl group substituted with halogen, instead of hydrogen or methyl.

Further, the substrate monomer is not particularly limited so long as it is in a form of e.g. a free acid, a metal salt of e.g. sodium or potassium, or an ammonium salt or a triethylamine salt. The formed hyaluronic acid or hyaluronic acid derivative depends on the form of the salt of glucuronic acid as the substrate monomer, and e.g. a free acid, a metal salt of e.g. sodium or potassium, an ammonium salt and a triethylamine salt are included.

When a batch reaction is started under the above conditions, the reaction is completed in several hours to several days, although it can not completely be defined depending upon the conditions. After completion of the reaction, the reaction liquid may be subjected to a combination of known purification means such as centrifugal separation, ultrafiltration, microfiltration, various adsorbent columns, solvent precipitation and separation by chromatography to isolate and purify hyaluronic acid with a high purity. The hyaluronic acid or hyaluronic acid derivative thus obtained can be used widely as cosmetics, pharmaceutical products or biomedical materials.

Now, the present invention will be explained in detail with reference to Examples, but the present invention is by no means restricted to the following Examples.

EXAMPLE 1

Preparation of Benzyl 2-acetamido-2-deoxy-4,6-O-isopropylidene -3-O-(methyl 2',3',4'-tri-O-acetyl-β-D-glucopyranosyluronate) -β-D-glucopyranoside (3)

Into a light-resistant two-necked eggplant-type flask, benzyl 2-acetamido-2-deoxy-4,6-O-isopropylidene-β-D-glucopyranoside (1.067 g, 3.04 mmol) was put, and dichloromethane (30 ml) was added thereto to dissolve it. Silver trifluoromethanesulfonate (1.16 g, 4.51 mmol) and MS4A powder were added thereto. The solution was cooled to −40° C. with stirring in an atmosphere of argon, and a solution having methyl(2,3,4-tri-O-acetyl-α-glucopyranoside bromide)uronate (1.70 g, 4.28 mmol) dissolved in dichloromethane (10 ml) and 1,1,3,3-tetramethylurea (0.5 ml, 4.17 mmol) were dropwise added thereto. Then, stirring was carried out for 30 minutes at −40° C., and then the temperature was gradually recovered to room temperature, followed by stirring for 22 hours. After completion of the reaction was confirmed by TLC, the reaction solution was subjected to filtration by celite (No. 545) to remove insoluble matters, the filtrate was washed with a saturated sodium hydrogencarbonate aqueous solution (once) and a cooled saturated salt solution (three times) for liquid separation, and the organic layer was dried over anhydrous sodium sulfate overnight. Then, magnesium sulfate was removed by glass filter, and the filtrate was vacuum concentrated. The obtained residue was purified by flash silica gel column chromatography (elution mixed solvent: ethyl acetate/hexane=1:2, 1:1, 2:1), and the solvent after developing was vacuum dried. The obtained product was further isolated and purified by Sephadex™ LH-20 size exclusion column chromatography (eluent: methanol), and the solvent after developing was vacuum dried to obtain benzyl 2-acetamido-2-deoxy-4,6-O -isopropylidene-3-O-(methyl 2',3',4'-tri-O-acetyl-β-D -glucopyranosyluronate)-β-D-glucopyranoside (583 mg, 0.873 mmol, 29%).

Assignments of the NMR spectra are as follows.

$^1$H NMR (400 MHz, CDCl$_3$, TMS): δ (ppm): 7.34–7.26 (5H, m, aromatic), 5.70 (1H, d, $J_{2, N-H}$=7.15 Hz, NH), 5.24–5.15 (3H, m, H-3', H-1, H-4'), 4.95 (1H, t, $J_{1', 2'}$=$J_{2'-3'}$=8.09 Hz, H-2'), 4.86–4.83 (2H, m, H-1', CH$_2$Ph), 4.55–4.49 (2H, m, CH$_2$Ph, H-3), 3.96–3.92 (2H, m, H-5', H-6), 3.81–3.71 (5H, m, H-6, H-4, CH$_3$O of methyl ester), 3.38 (1H, m, H-5), 3.04 (1H, m, H-2), 2.09–2.00 (12H, m, Ac), 1.58 (3H, s, (CH$_3$)$_2$C), 1.41 (3H, s, (CH$_3$)$_2$C)

$^{13}$C NMR (100 MHz, CDCl$_3$, TMS): δ (ppm): 170.35–169.48 (CH$_3$CO), 167.29 (C-6'), 136.61–128.06 (aromatic), 99.64 (C-1'), 99.42 ((CH$_3$)$_2$C, 98.59 (C-1), 77.00 (C-3), 73.87 (C-4), 72.66 (C-5'), 72.34 (C-3'), 71.71, 71.65 (C-2', CH$_2$Ph), 69.47 (C-4'), 66.51 (C-5), 62.08 (C-6), 58.39 (C-2), 52.85 (CH$_3$O), 29.08 ((CH$_3$)$_2$C), 23.59 (NHCOCH$_3$), 20.75–20.49 (OCOCH$_3$), 18.51 ((CH$_3$)$_2$C)

EXAMPLE 2

Preparation of 2-acetamido-2-deoxy-3-O-(methyl 2',3',4'-tri-O-acetyl-β-D-glucopyranosyluronate)-D-glucopyranose (4)

In an eggplant-type flask, benzyl 2-acetamido-2-deoxy-4,6-O-isopropylidene-3-O-(methyl 2',3',4'-tri-O-acetyl-β-D-glucopyranosyluronate)-β-D-glucopyranoside (488 mg, 0.731 mmol) was dissolved in a dichloromethane/methanol (1:1, v/v) mixed solvent (180 ml), and 10% palladium carbon (190 mg) was added thereto, followed by reaction at room temperature for 72 hours in an atmosphere of hydrogen. After completion of the reaction was confirmed by TLC, the palladium carbon was removed by filtration with celite, and the filtrate was vacuum concentrated. The obtained residue was re-precipitated from diisopropyl ether and vacuum dried to obtain 2-acetamido-2-deoxy-3-O-(methyl 2',3',4'-tri-O-acetyl-β-D-glucopyranosyluronate)-D-glucopyranose (383 mg, 0.713 mmol, 98%).

Assignments of the NMR spectra are as follows.

$^1$H NMR (400 MHz, CD$_3$OD): δ (ppm): 5.29 (1H, t, $J_{2', 3'}$=$J_{3',4'}$=9.32 Hz, H-3'), 5.10 (1H, t, $J_{3',4'}$=$J_{4', 5'}$=9.71 Hz, H-4'), 4.99 (1H, d, $J_{1,2}$=3.49 Hz, H-1α), 4.95 (1H, t, $J_{1', 2'}$=$J_{2',3'}$=8.68 Hz, H-2'), 4.84 (1H, d, $J_{1', 2'}$=7.98 Hz, H-1'), 4.25 (1H, d, $J_{4', 5'}$=9.96 Hz, H-5'), 3.98 (1H, m, H-2α), 3.84–3.77 (3H, m, H-3α, H-6α, H-5α), 3.72 (3H, s, CH$_3$O of methyl ester), 3.71–3.68 (1H, m, H-6α), 3.45 (1H, t, $J_{3',4'}$=$J_{4', 5'}$=9.18 Hz, H-4α), 2.04–1.95 (12H, m, Ac)

$^{13}$C NMR (100 MHz, CD$_3$OD): δ (ppm): 175–171 (CH$_3$CO), 168.83 (C-6'), 101.01 (C-1'), 92.34 (C-1α), 81.94 (C-3α), 73.07 (C-3'), 72.42, 72.25, 72.00 (C-5α, C-2', C-5'), 70.42 (C-4'), 69.98 (C-4α), 62.59 (C-6α), 53.73, 53.63 (C-2α, CH$_3$O of methyl ester), 23.14 (NHCOCH$_3$), 20.86–20.76 (OCOCH$_3$)

EXAMPLE 3

Preparation of 2-acetamido-4,6-di-O-acetyl-2-deoxy-3-O-(methyl 2',3',4'-tri-O-acetyl-β-D-glucopyranosyluronate) -D-glucopyranosyl acetate (5)

In a two-necked eggplant-type flask, 2-acetamido-2-deoxy-3-O-(methyl 2',3',4'-tri-O-acetyl-β-D-glucopyranosyluronate)-D-glucopyranose (447 mg, 0.832 mmol) was dissolved in pyridine (10 ml) having 4-dimethylaminopyridine (13.6 mg, 0.111 mmol) dissolved therein, and acetic anhydride (5 ml, 53.0 mmol) was dropwise added thereto in a dry atmosphere, followed by stirring at 0° C. for 6 hours. After completion of the reaction was confirmed by TLC, the reaction solution was vacuum concentrated, the residue was diluted with chloroform and washed with 0.1 M hydrochloric acid (once), a saturated sodium hydrogencarbonate aqueous solution (once) and a saturated salt solution (three times) for liquid separation, and the organic layer was dried over anhydrous sodium sulfate overnight. Then, magnesium sulfate was removed by filtration with glass filter, the filtrate was vacuum concentrated and the residue was dissolved in ethyl acetate, re-precipitated from diisopropyl ether and vacuum dried to obtain 4,6-di-O-acetyl-2-acetamido-2-deoxy-3-O-(methyl 2',3',4'-tri-O-acetyl-β-D-glucopyranosyluronate)-D-glucopyranosyl acetate (543 mg, 0.818 mmol, 98%).

Assignments of the NMR spectra are as follows.

$^1$H NMR (400 MHz, CDCl$_3$, TMS): δ (ppm): 6.06 (1H, d, $J_{1,2}$=3.63 Hz, H-1α), 5.32 (1H, d, $J_{2, N-H}$=9.74 Hz, NH), 5.26 (1H, t, $J_{2', 3'}$=$J_{3', 4'}$=9.34 Hz, H-3'), 5.16–5.06 (2H, m, H-4', H-4α), 4.82 (1H, t, $J_{1', 2'}$=$J_{2', 3'}$=8.52 Hz, H-2'), 4.73 (1H, d, $J_{1', 2'}$=7.79 Hz, H-1'), 4.55 (1H, m, H-2α), 4.20 (1H, dd, H-6α), 4.06 (1H, dd, H-6α), 4.03 (1H, d, $J_{4', 5'}$=10.00 Hz, H-5'), 3.97 (1H, m, H-5α), 3.94 (1H, t, $J_{2, 3}$=$J_{3, 4}$=9.81 Hz, H-3α), 3.75 (3H, s, CH$_3$O of methyl ester), 2.20–2.01 (21H, m, CH$_3$CO of acetate and acetamide)

$^{13}$C NMR (100 MHz, CDCl$_3$, TMS): δ (ppm): 170.82–168.67 (CH$_3$CO), 167.00 (C-6'), 100.39 (C-1'), 91.34 (C-1α), 76.42 (C-3α), 72.60 (C-5'), 71.84 (C-3'), 71.57 (C-2'), 69.87 (C-5α), 69.54 (C-4'), 67.63 (C-4α), 61.69 (C-6α), 52.88 (CH$_3$O), 51.12 (C-2α), 23.42 (NHCOCH$_3$), 21.04–20.48 (OCOCH$_3$)

EXAMPLE 4

Preparation of 2-methyl[4,6-di-O-acetyl-1,2-dideoxy-3-O-(methyl 2',3',4'-tri-O-acetyl-β-D-glucopyranosyluronate)-α-D-glucopyrano]-[2,1-d]-2-oxazoline (6)

In a two-necked eggplant-type flask, in an atmosphere of argon, 2-acetamido-4,6-di-O-acetyl-2-deoxy-3-O-(methyl 2',3',4'-tri-O-acetyl-β-D-glucopyranosyluronate) -D-glucopyranosyl acetate (343 mg, 0.517 mmol) was dissolved in 1,2-dichloroethane (120 ml), and trimethylsilyl trifluoromethanesulfonate (0.14 ml, 0.843 mmol) diluted with 1,2-dichloroethane (0.5 ml) was dropwise added thereto, followed by reaction at 50° C. for 7 hours. Completion of the reaction was confirmed by TLC, and triethylamine (0.12 ml, 0.889 mmol) was dropwise added thereto under cooling with ice, followed by stirring at room temperature for 30 minutes to terminate the reaction. Then, the reaction solution was vacuum concentrated, the residue was purified by flash silica gel column chromatography (elution mixed solvent: chloroform/methanol=20:1, 15:1, 10:1), the solvent after developing was vacuum concentrated, and the obtained colorless oily matter was evaporated to dryness under reduced pressure. The obtained product was further subjected to Sephadex LH-20 size exclusion column chromatography (eluent: methanol), and the solvent after developing was concentrated by evaporation and vacuum dried to obtain colorless amorphous 2-methyl-[4,6-di-O-acetyl -1,2-dideoxy-3-O-(methyl 2',3',4'-tri-O-acetyl-β-D-glucopyranosyluronate)-α-D-glucopyrano]-[2,1-d]-2-oxazoline (311 mg, 0.515 mmol) quantitatively.

Assignments of the NMR spectra are as follows.

$^1$H NMR (400 MHz, CDCl$_3$, TMS): δ (ppm): 5.96 (1H, d, J$_{1, 2}$=6.69 Hz, H-1), 5.30–5.19 (3H, m, H-3', H-4', H-4), 5.00 (1H, t, J$_{1', 2'}$=J$_{2', 3'}$=8.31 Hz, H-2'), 4.92 (1H, d, J$_{1', 2'}$=7.24 Hz, H-1'), 4.18–4.15 (3H, m, H-6, H-6, H-5'), 4.13 (1H, s, H-3), 4.06 (1H, m, H-2), 3.75 (3H, s, CH$_3$O of methyl ester), 3.61 (1H, m, H-5), 2.12–2.02 (18H, m, Ac and CH$_3$C of oxazoline)

$^{13}$C NMR (100 MHz, CDCl$_3$, TMS): δ (ppm): 170.81–169.18 (OCOCH$_3$), 167.08–166.59 (CH$_3$C of oxazoline, C-6'), 100.77 (C-1'), 99.70 (C-1), 78.37 (C-3), 72.28 (C-5'), 72.17 (C-3'), 71.14 (C-2'), 69.11 (C-4'), 67.75 (C-4), 47.41 (C-5), 65.52 (C-2), 63.56 (C-6), 52.81 (CH$_3$O), 20.93–20.50 (OCOCH$_3$), 14.05 (CH$_3$C of oxazoline)

High resolution FAB Mass.
Calculated value: [M+H]$^+$=604.1878 m/z (C$_{25}$H$_{34}$NO$_{16}$).
Measured value: 604.1851 m/z (−4.5 ppm).

EXAMPLE 5

Preparation of 2-methyl-[1,2-dideoxy-3-O-(sodium β-D-glucopyranosyluronate)]-α-D-glucopyrano-[2,1-d]-2-oxazoline (8)

In a two-necked eggplant-type flask, 2-methyl[4,6-di-O-acetyl-1,2-dideoxy-3-O-(methyl 2',3',4'-tri-O-acetyl -β-D-glucopyranosyluronate)-α-D-glucopyrano[2,1-d]-2-oxazoline (72.4 mg, 0.120 mmol) was dissolved in methanol (5.0 ml) in an atmosphere of argon, and a 0.1M sodium methoxide/methanol solution (0.3 ml, 0.0300 mmol) was gradually added thereto under cooling with ice, followed by stirring at room temperature for 30 minutes. Completion of the reaction was confirmed by TLC, and then the reaction solution was concentrated by evaporation and evaporated to dryness under reduced pressure. The obtained product was dissolved in a 50 mM carbonic acid buffer solution (1.080 ml, pH 10.6), followed by stirring at room temperature for 30 minutes to obtain 2-methyl-[1,2-dideoxy-3-O-(sodium β-D-glucopyranosyluronate)-α-D-glucopyrano[2,1-d]-2-oxazoline.

The analysis data are as follows.

$^1$H NMR (400 MHz, 50 mM carbonic acid buffer heavy water solution (pH 10.6): δ (ppm): 6.07 (1H, d, J$_{1, 2}$=7.14 Hz, H-1), 4.62 (1H, d, J$_{1', 2'}$=7.36 Hz, H-1'), 5.30–5.19 (3H, m, H-3', H-4', H-4), 5.00 (1H, t, J$_{1', 2'}$=J$_{2', 3'}$=8.31 Hz, H-2'), 4.92 (1H, d, J$_{1', 2'}$=7.36 Hz, H-1'), 4.26 (1H, m, H-2), 4.10 (1H, s, H-3), 3.82–3.71 (3H, m, H-4, H-6, H-5'), 3.64 (1H, dd, J$_{5, 6}$=6.31 Hz, J$_{6, 6}$=12.29 Hz, H-6), 3.49–3.47 (2H, m, H-3', H-4'), 3.33–3.26 (2H, m, H-5, H-2'), 2.02 (3H, s, CH$_3$C of oxazoline)

$^{13}$C NMR (100 MHz, 50 mM carbonic acid buffer heavy water solution (pH 10.6): δ (ppm): 175.97 (C-6'), 168.52 (CH$_3$C of oxazoline), 101.84 (C-1'), 100.39 (C-1), 79.19 (C-3), 75.99 (C-5'), 75.47 (C-3'), 72.86 (C-2'), 72.33 (C-5), 71.85 (C-4'), 67.79 (C-4), 64.14 (C-2), 61.61 (C-6), 13.15 (CH$_3$C of oxazoline)

High resolution FAB Mass.
Calculated value: [M+H]$^+$=402.1012 m/z (C$_{25}$H$_{34}$NO$_{16}$).
Measured value: 402.1014 m/z (+0.5 ppm).

EXAMPLE 6

Preparation of hyaluronic acid by enzyme-catalyzed polymerization

Of a solution having 2-methyl-[1,2-dideoxy-3-O-(sodium β-D-glucopyranosyluronate)-α-D-glucopyrano[2,1-d]-2-oxazoline (48.2 mg, 0.12 mmol) obtained in Example 5 as a substrate monomer dissolved in a heavy water carbonic acid buffer solution (1.080 ml), pH was adjusted to 7.1 by a DCl heavy water solution (1.0 mol/l, 0.5 mol/l, 0.1 mol/l). 360 μl of this solution was put in each of NMR sample tubes (Entries 1 to 3), and variation with time at 30° C. was measured by $^1$H NMR. Heavy water (40 μl) in Entry 1, a solution having bovine testicular hyaluronidase (1.6 mg) (SIGMA, Lot No. 77H7065, 330 units/mg) dissolved in heavy water (40 μl) in Entry 2 and a solution having ovine testicular hyaluronidase (1.6 mg) (ICN Biomedicals Inc., Lot No. 9303B, 560 units/mg) dissolved in heavy water (40 μl) in Entry 3 were put into the respective sample tubes, followed by well stirring, and the variation with time at 30° C. was measured again by $^1$H NMR. Methyl proton of the acetamide group was taken as the internal standard, and the ratio of its integrated value to the integrated value of the reducing terminal 1-position proton of the oxazoline monomer was obtained to calculate the variation with time of the substrate monomer concentration.

The results are shown in the following Table 1 and FIG. 2.

TABLE 1

| | Residual ratio of substrate monomer | | |
|---|---|---|---|
| Time | Residual ratio (%) | | |
| (hr) | Entry 1 | Entry 2 | Entry 3 |
| 0 | 100 | 100 | 100 |
| 1 | 95.6 | 98.3 | 98.9 |
| 2 | 96.5 | 101 | 96.6 |
| 3 | 95.6 | 98.6 | 96.7 |
| 4 | 99.7 | 97.3 | 99.6 |
| 5 | 96.6 | 88.5 | 76.5 |
| 6 | 93.9 | 85.1 | 65.6 |
| 7 | 94.9 | 81.9 | 62.1 |
| 8 | 89.8 | 79.9 | 60.2 |
| 9 | 90.5 | 76.9 | 54.3 |
| 10 | 88 | 75.8 | 51.3 |
| 11 | 85.7 | 75 | 52.1 |
| 12 | 84 | 71.7 | 45.2 |
| 15 | 77 | 66 | 35.7 |
| 18 | 71.4 | 56.1 | 21.8 |
| 21 | 67.3 | 50.2 | 15.4 |
| 24 | 59.7 | 44.1 | 12.2 |
| 40 | 44.6 | 13.9 | 2.3 |
| 48 | 27.3 | 14.1 | — |
| 64 | 27.3 | 4.6 | — |

Figure 2:
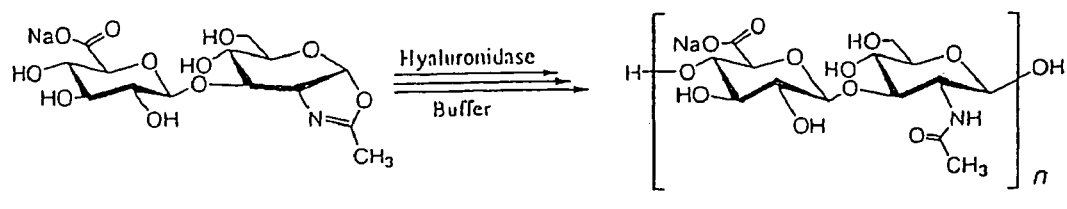
FIG. 2 illustrates a variation with time of a monomer substrate in a reaction liquid.
Figure 2:
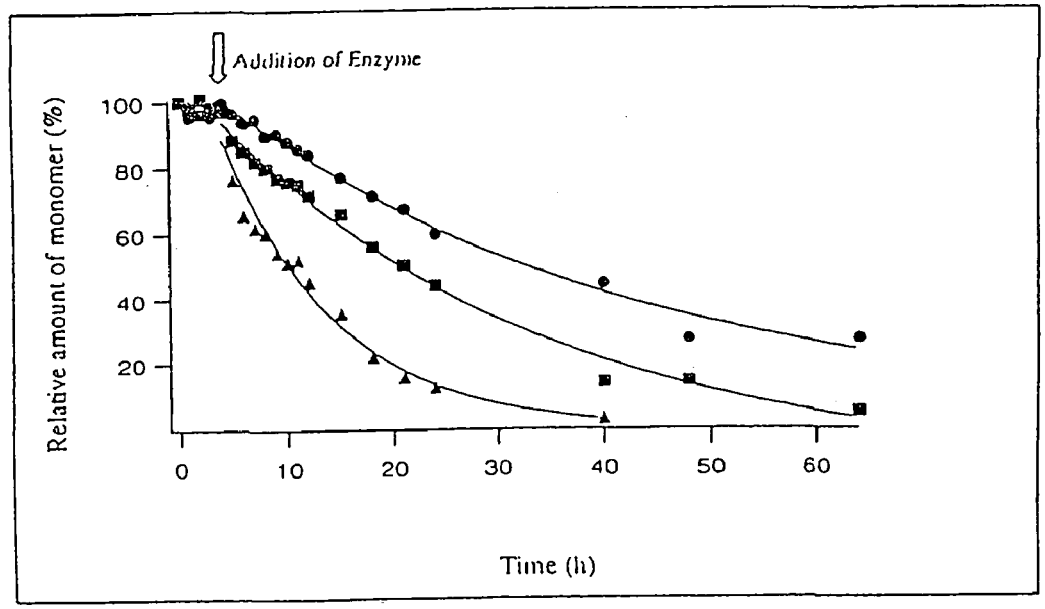

As evident from the results shown in the above Table 1 and FIG. 2, it becomes clear that in systems in which bovine or ovine testicular hyaluronidase is added, the monomer consumption is significantly accelerated as compared with a system in which no hyaluronidase is added, and it becomes clear that the hyalobiuronate oxazoline derivative is recognized by both enzymes and ring-opening reaction of the oxazoline ring takes place.

Figure 3:
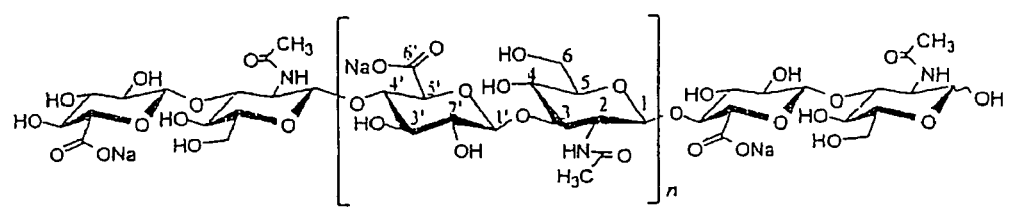
FIG. 3 illustrates $^1$H NMR spectrum of formed hyaluronic acid.
Figure 3:
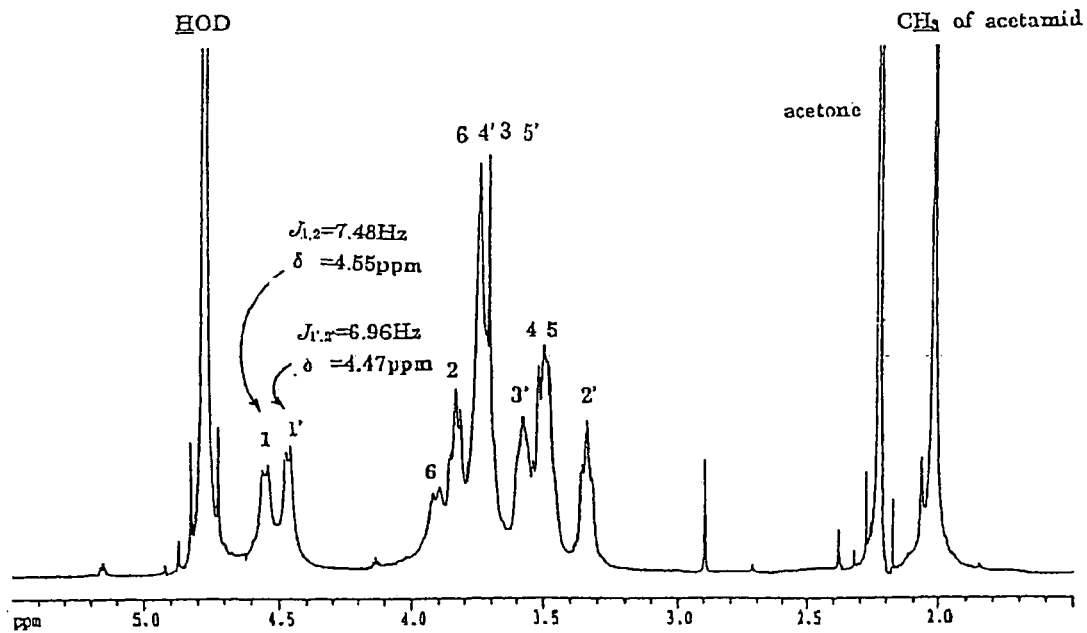
Figure 4:
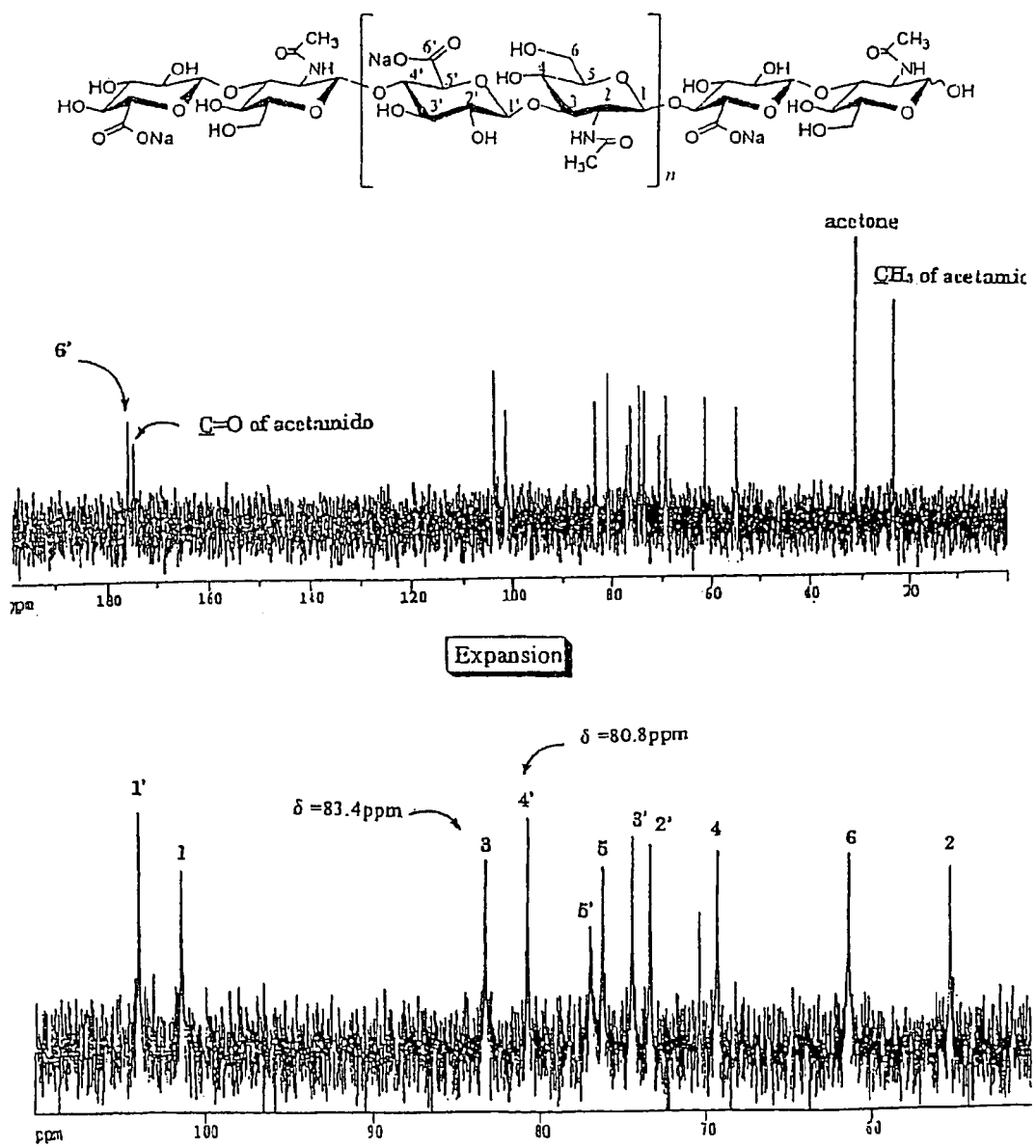
FIG. 4 illustrates a $^{13}$C NMR spectrum of formed hyaluronic acid.

In systems in which the hyaluronidase was added (Entries 2, 3), after it was confirmed that the monomer consumption was completed, the polymer solution was soaked in a water bath of 90° C. for 3 minutes, whereby the enzyme was deactivated to terminate the reaction. THF (5.0 ml) was added to the solution, the precipitated deposit was separated by centrifugal separation and vacuum dried to obtain a product. The obtained product was dissolved in distilled water and purified by size exclusion column chromatography (Sephadex™ G-10), and the solvent after developing was freeze dried to obtain a product. The obtained product was analyzed by $^1$H NMR, $^{13}$C NMR and GPC measurement. $^1$H NMR spectrum, $^{13}$C NMR spectrum and the results by GPC measurement are shown in FIG. 3, FIG. 4 and Table 2, respectively. As NMR tubes, Symmetrical Microtube Matched with aqueous solution, BMS-005B manufactured by Shigemi Inc. were employed. For $^1$H NMR measurement, about 5.0 mg of the sample was dissolved in heavy water (200 μl), and measurement was carried out at 25° C. $^{13}$C NMR measurement was carried out at 40° C. at a concentration of about 5.0 mg of the product in heavy water (100 μl). For the internal standard substance, acetone (2 μl) was employed, and corrections to 2.225 ppm and 31.07 ppm were carried out for $^1$H NMR and $^{13}$C NMR, respectively.

$^1$H NMR (400 MHz, D$_2$O, Acetone): δ (ppm): 4.55 (1H, d, $J_{1,2}$=7.48 Hz, H-1), 4.47 (1H, d, $J_{1',2'}$=6.96 Hz, H-1'), 3.92–3.70 (6H, m, H-6, H-2, H-6, H-4', H-3, H-5'), 3.58–3.50 (3H, m, H-3', H-4, H-5), 3.34 (1H, t, H-2'), 2.02 (3H, s, NHCOCH$_3$)

$^{13}$C NMR (100 MHz, D$_2$O, Acetone): δ (ppm): 175.70 (C-6'), 174.53 (NHCOCH$_3$), 103.89 (C-1'), 101.34 (C-1), 83.43 (C-3), 80.79 (C-4'), 76.98 (C-5'), 76.25 (C-5), 74.46 (C-3'), 73.31 (C-2'), 69.33 (C-4), 61.43 (C-6), 55.11 (C-2), 23.31 (NHCOCH$_3$)

As the standard substance for GPC measurement, sodium hyaluronates (Mn=800, 2000, 4000, Mv=50000*, 100000*) were employed. The measurement conditions are as follow.

| Conditions of liquid chromatography | |
|---|---|
| Detector: | differential detector |
| Column: | Shodex Ohpak SB-803HQ |
| Guard column: | Shodex Ohpak SB-G |
| Column temperature: | 40° C. |
| Mobile phase: | 0.1M sodium nitrate |
| Flow rate: | 0.5 ml/min |
| Injection amount: | 20 μl |

*: Regarding sodium hyaluronates having Mv of 50000 and 100000, their Mn was calculated by GPC measurement.

TABLE 2

Yield and molecular weight of formed hyaluronic acid

|  | Yield (%) | Mn (× 10000) | Mw (× 10000) | Mw/Mn |
|---|---|---|---|---|
| Bovine testicular hyaluronidase | 39 | 1.74 | 6.69 | 3.84 |
| Ovine testicular hyaluronidase | 52 | 1.35 | 4.12 | 3.05 |

EXAMPLE 7

Follow-up on Enzyme-catalyzed Polymerization Behavior

Of a solution having 2-methyl-[1,2-dideoxy-3-O-(sodium β-D-glucopyranosyluronate)-α-D-glucopyrano[2,1-d]-2-oxazoline (84.4 mg, 0.21 mmol) obtained in Example 5 as a substrate monomer dissolved in a carbonic acid buffer solution (2.0 ml), pH was adjusted to 7.1 (Entries 1, 2), 8.0 (Entries 3, 4) or 9.0 (Entries 5, 6) by a HCl aqueous solution (1.0 mol/l, 0.5 mol/l, 0.1 mol/l), and 630 μl of each of the solutions was put in an Eppendorf tube. Further, 210 μl of each of these solutions was put in an Eppendorf tube, and a solution having bovine testicular hyaluronidase (0.9 mg) dissolved in distilled water (10 μl) (Entries 1, 3, 5) or a solution having ovine testicular hyaluronidase (0.9 mg) dissolved in heavy water (10 μl) (Entries 2, 4, 6) was added to the Eppendorf tube, and the reaction was started at 30° C. In each Entry, 20 μl of the reaction solution was collected 0, 3, 6, 9, 12, 24, 36, 48, 72, 96 and 120 hours after initiation of the reaction, and solutions having these reaction solutions diluted with 40 μl of distilled water were subjected to GPC analysis.

Figure 5:
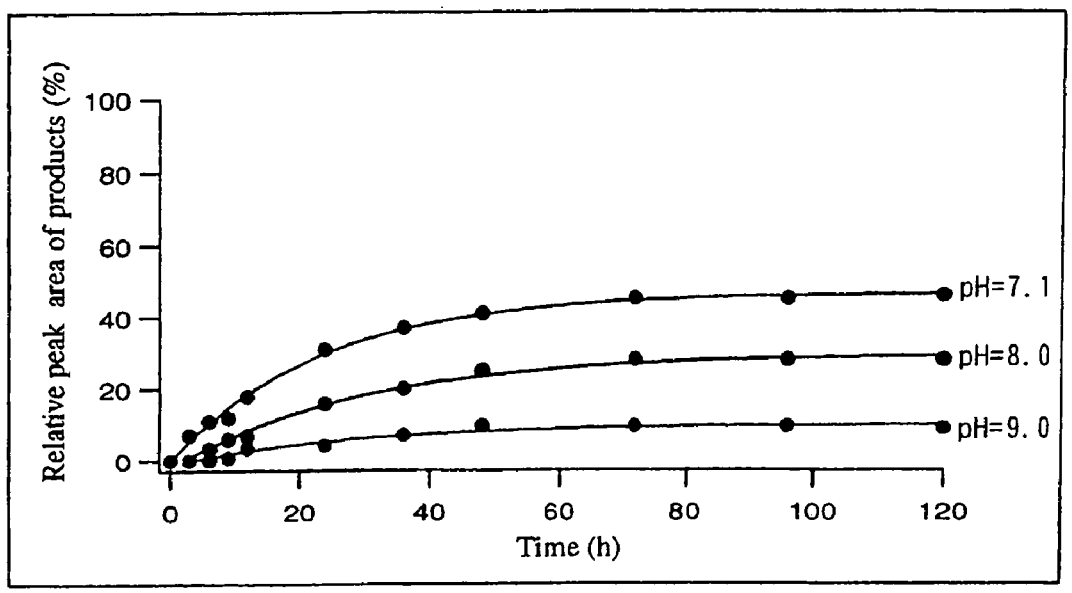
FIG. 5 illustrates influences of pH in a case of bovine testicular hyaluronidase and in a case of ovine testicular hyaluronidase.
Figure 5:
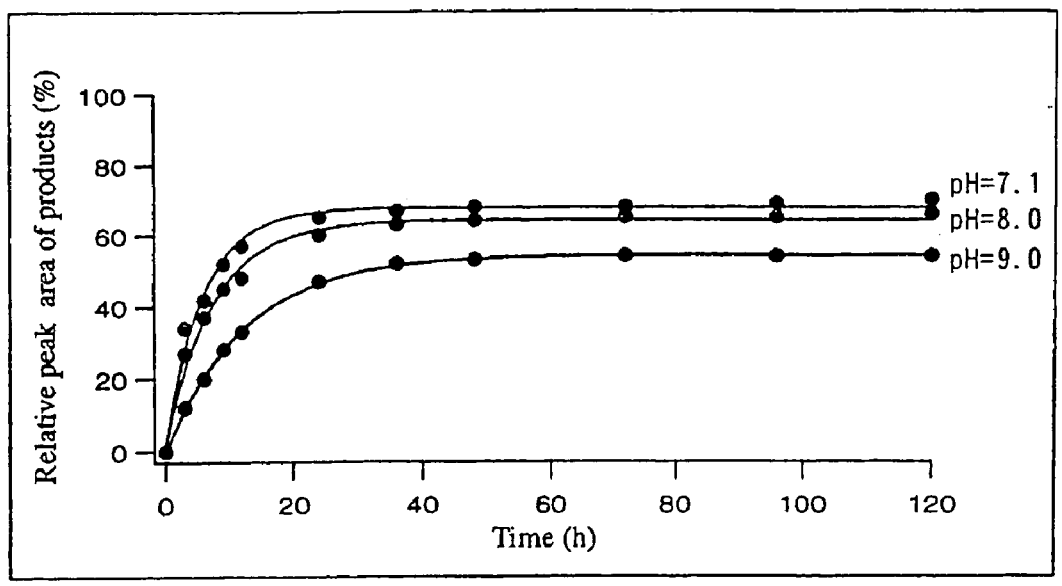

The results are shown in Tables 3 and 4 and FIG. 5.

TABLE 3

Results when bovine testicular hyaluronidase is employed

| | Relative peak area (%) | | |
|---|---|---|---|
| Time (hr) | pH = 7.1 (Entry 1) | pH = 8.0 (Entry 3) | pH = 9.0 (Entry 5) |
| 0 | 0 | 0 | 0 |
| 3 | 7.1 | 0 | 0 |
| 6 | 11 | 3.4 | 0 |
| 9 | 12 | 6.1 | 0.8 |
| 12 | 18 | 6.9 | 3.5 |
| 24 | 31 | 16 | 4.3 |
| 36 | 37 | 20 | 7.1 |
| 48 | 41 | 25 | 9.7 |
| 72 | 45 | 28 | 9.5 |
| 96 | 45 | 28 | 9.5 |
| 120 | 46 | 28 | 8.8 |

TABLE 4

Results when ovine testicular hyaluronidase is employed

| | Relative peak area (%) | | |
|---|---|---|---|
| Time (hr) | pH = 7.1 (Entry 2) | pH = 8.0 (Entry 4) | pH = 9.0 (Entry 6) |
| 0 | 0 | 0 | 0 |
| 3 | 34 | 27 | 12 |
| 6 | 42 | 37 | 20 |
| 9 | 52 | 45 | 28 |
| 12 | 57 | 48 | 33 |
| 24 | 65 | 60 | 47 |
| 36 | 67 | 63 | 52 |
| 48 | 68 | 64 | 53 |
| 72 | 68 | 65 | 54 |
| 96 | 69 | 65 | 54 |
| 120 | 70 | 66 | 54 |

EXAMPLE 8

Preparation of Benzyl 2-azido-4,6-O-benzylidene-2-deoxy-3-O-(Methyl 2,3,4-tri-O-acetyl-β-D-glucopyranosyluronate)-β-D-glucopyranoside In a light-resistant two-necked flask, methyl(2,3,4-tri-O-acetyl-α-D-glucopyranoside trichloroacetoimidate)uronate (502 mg, 1.05 mmol) and benzyl 2-azido-4,6-O-benzylidene-2-deoxy-β-D-glucopyranoside (200 mg, 0.522 mmol) were dissolved in dichloromethane (3.00 ml), activated molecular sieves 4A (MS4A: 360 mg) were added thereto, and trimethylsilyl trifluoromethanesulfonate (TMSOTf: 188 μl, 0.939 mmol) was gradually added thereto in an atmosphere of argon at −20° C., followed by stirring for 40 minutes. After completion of the reaction, triethylamine (0.200 ml, 1.48 mmol) was added thereto at −20° C., and insoluble matters were removed by filtration with celite. Then, the filtrate was diluted with chloroform, and washed with a saturated sodium hydrogencarbonate aqueous solution and a saturated salt solution in this order. The organic layer was dried over anhydrous magnesium sulfate, and insoluble matters were removed by filtration with celite. The filtrate was vacuum concentrated, and the obtained residue was purified by flash silica gel column chromatography (elution solvent: n-hexane/ethyl acetate 5/1–3/1) and then by Sephadex LH-20 size exclusion chromatography to obtain white powdery benzyl 2-azido-4,6-O-benzylidene-2-deoxy-3-O-(methyl 2,3,4-tri-O-acetyl-β-D-glucopyranosyluronate)-β-D-glucopyranoside (117 mg, 0.167 mmol, 32%).

The analysis data are as follows.

$^1$H NMR (400 MHz, CDCl$_3$, TMS): δ (ppm); 7.43–7.31 (10H, m, aromatics), 5.52 (1H, s, CHPh), 5.21 (1H, t, J=9.29 Hz, H-3'), 5.16 (1H, t, J=9.29 Hz, H-4'), 5.04 (1H, t, J=8.53 Hz, H-2'), 4.93 (1H, d, J=11.55 Hz, CH$_2$Ph), 4.78 (1H, d, J=7.53 Hz, H-1'), 4.69 (1H, d, J=12.05 Hz, CH$_2$Ph), 4.46 (1H, d, J=8.03 Hz, H-1), 4.34 (1H, dd, J=5.02, 10.54 Hz, H-6a), 3.84–3.77 (2H, m, H-6b, H-5'), 3.72 (1H, t, J=9.04 Hz, H-4), 3.62 (1H, t, J=9.29 Hz, H-3), 3.58 (3H, s, COOCH$_3$), 3.46 (1H, dd, J=8.03, 9.53 Hz, H-2), 3.36 (1H, dt, J=5.02, 9.54 Hz, H-5), 2.06 (3H, s, Ac), 2.00 (3H, s, Ac), 1.98 (3H, s, Ac)

High resolution FAB MS.
Calculated value: [M+H]$^+$=699.67 m/z (C$_{33}$H$_{37}$N$_3$O$_{14}$).
Measured value: 700 m/z.

EXAMPLE 9

Preparation of Benzyl 2-azido-2-deoxy-3-O-(methyl 2,3,4-tri-O-acetyl-β-D-glucopyranosyluronate)-β-D-glucopyranoside In an eggplant-type flask, benzyl 2-azido-4,6-O-benzylidene-2-deoxy-3-O-(methyl 2,3,4-tri-O-acetyl-β-D-glucopyranosyluronate)-β-D-glucopyranoside (199 mg, 0.285 mmol) was dissolved in a 90% acetic acid aqueous solution (5.00 ml), followed by reaction at 70° C. for 3 hours for deblocking of the benzylidene group. After completion of the reaction, extraction of ethyl acetate was carried out, and washing with a saturated sodium hydrogencarbonate aqueous solution and a saturated salt solution was carried out for liquid separation. The organic layer was dried over anhydrous magnesium sulfate, and insoluble matters were removed by filtration with celite. The filtrate was vacuum concentrated, and the residue was purified by flash silica gel column chromatography (elution solvent: n-hexane/ethyl acetate 1/1–1/4) to obtain white powdery benzyl 2-azido-2-deoxy-3-O-(methyl 2,3,4-tri-O-acetyl-β-D-glucopyranosyluronate)-β-D-glucopyranoside (107 mg, 0.175 mmol, 61%).

The analysis data are as follows.

$^1$H NMR (400 MHz, CDCl$_3$, TMS): δ (ppm): 7.38–7.27 (5H, m, aromatics), 5.30 (1H, t, J=9.53 Hz, H-3'), 5.20 (1H, t, J=9.54 Hz, H-4'), 5.04 (1H, dd, J=8.03, 9.53 Hz, H-2'), 4.91 (1H, d, J=12.05 Hz, CH$_2$Ph), 4.72 (1H, d, J=12.05 Hz, CH$_2$Ph), 4.68 (1H, d, J=8.03 Hz. H-1'), 4.39 (1H, d, J=8.03 Hz, H-1), 4.07 (1H, d, J=10.04 Hz, H-5'), 3.97–3.91 (1H, m, H-6a), 3.90 (1H, s, 4-OH), 3.81–3.74 (4H, m, H-6b, COOCH$_3$), 3.56 (1H, bt, J=9.29 Hz, H-4), 3.38 (1H, dd, J=8.03, 9.54 Hz, H-2), 3.30–3.27 (1H, m, H-5), 3.23 (1H, t, J=9.29 Hz, H-3), 2.09 (3H, s, Ac), 2.04 (3H, s, Ac), 2.03 (3H, s, Ac), 1.98 (1H, bt, J=6.78 Hz, 6-OH)

High resolution FAB MS.
Calculated value: [M+H]$^+$=611.56 m/z (C$_{26}$H$_{33}$N$_3$O$_{14}$).
Measured value: 612 m/z.

EXAMPLE 10

Preparation of 4,6-di-O-acetyl-2-deoxy-3-O-(methyl 2,3,4-tri-O-acetyl-β-D-glucopyranosyluronate)-2-propanamido-D-glucopyranosyl acetate In a two-necked eggplant-type flask, benzyl 2-azido-2-deoxy-3-O-(methyl 2,3,4-tri-O-acetyl-β-D-glucopyranosyluronate)-β-D-glucopyranoside (101 mg, 0.165 mmol) was dissolved in methanol (6.00 ml), and 20% palladium hydroxide activated carbon (100 mg) was added thereto to carry out catalytic hydrogen reduction in an atmosphere of hydrogen for 27 hours for deblocking of the benzyl group and conversion of the azide group to an amino group. After completion of the reaction, insoluble matters were removed by filtration with celite, and the celite bed was washed with methanol (12.0 ml). Triethylamine (0.100 ml, 0.741 mmol) was added to the filtrate, and propionyl chloride (22.0 μl, 0.252 mmol) was added thereto in a dry atmosphere at 0° C., followed by reaction for 3 hours. After completion of the reaction, pyridine (4.00 ml) was added thereto, followed by vacuum concentration to remove methanol, and then acetic anhydride (3.00 ml, 31.5 mmol) was added thereto, followed by stirring at 0° C. for 1 hour and then at room temperature for 8 hours. After completion of the reaction, ice water was added to the reaction solution to decompose an excess amount of acetic anhydride, followed by vacuum concentration. The residue was extracted with ethyl acetate and washed with 1M hydrochloric acid, a saturated sodium hydrogencarbonate aqueous solution and a saturated salt solution in this order for liquid separation. The organic layer was dried over anhydrous magnesium sulfate and insoluble matters were removed by filtration with celite, and then the filtrate was vacuum concentrated. The obtained residue was purified by flash silica gel column chromatography (elution solvent: n-hexane/ethyl acetate 1/1–0/1) to obtain colorless oily matter 4,6-di-O-acetyl-2-deoxy-3-O-(methyl 2,3,4-tri-O-acetyl-β-D-glucopyranosyluronate)-2-propanamido-D-glucopyranosyl acetate (54.0 mg, 0.0790 mmol, 48%, α/β=73/27).

The analysis data are as follows.

$^1$H NMR for α form (400 MHz, CDCl$_3$, TMS): δ (ppm): 6.05 (1H, d, J=4.02 Hz, H-1), 5.25–5.02 (4H, m, NH, H-4, H-3', H-4'), 4.84 (1H, dd, J=7.53, 9.54 Hz, H-2'), 4.68 (1H, d, J=7.53 Hz, H-1'), 4.57 (1H, ddd, J=4.02, 10.04, 10.29 Hz, H-2), 4.20 (1H, dd, J=4.02, 12.55 Hz, H-6a), 4.07 (1H, m, H-6b), 4 02 (1H, d, J=10.04 Hz, H-5'), 3 98 (1H, m, H-5), 3 92 (1H, dd, J=10.04 Hz, H-3), 3.75 (3H, s, COOCH$_3$), 2.22 (2H, q, J=7.53 Hz, —CH$_2$CH$_3$), 2.20–2.00 (18H, m, Ac), 1.26 (3H, t, J=7.53 Hz, —CH$_2$CH$_3$)

High resolution FAB MS.
Calculated value: [M+H]$^+$=677.61 m/z (C$_{28}$H$_{39}$NO$_{18}$).
Measured value: 678 m/z.

EXAMPLE 11

Preparation of 2-ethyl-[4,6-di-O-acetyl-1,2-di-deoxy-3-O-(Methyl 2,3,4-tri-O-acetyl-β-D-glucopyranosyluronate)-α-D-glucopyrano]-[2,1-d]-2-oxazoline Employing a two-necked flask, in an atmosphere of argon, TMSOTf (20.0 μl, 0.120 mmol) was acted on 4,6-di-O-acetyl-2-deoxy-3-O-(methyl 2,3,4-tri-O-acetyl-β-D-glucopyranosyluronate)-2-propanamido-D-glucopyranosyl acetate (54.0 mg, 0.0790 mmol) in 1,2-dichloroethane (3.00 ml) at 50° C. 4.5 hours later, completion of the reaction was confirmed, and the reaction solution was cooled to 0° C. and triethylamine (40.0 μl, 0.300 mmol) was added thereto. Then, the reaction solution was vacuum concentrated, and the residue was purified by flash silica gel column chromatography (elution solvent: chloroform/methanol 40/1) and then by Sephadex LH-20 size exclusion chromatography to obtain colorless oily matter 2-ethyl-[4,6-di-O-acetyl-1,2-di-deoxy-3-O-(methyl 2,3,4-tri-O-acetyl-β-D-glucopyranosyluronate)-α-D-glucopyrano]-[2,1-d]-2-oxazoline (27.0 mg, 0.0440 mmol, 55%).

Assignments of an NMR spectrum are as follows.
$^1$H NMR (400 MHz, CDCl$_3$, TMS): δ (ppm): 5.96 (1H, d, J=7.52 Hz, H-1), 5.30–5.18 (3H, m, H-4, H-3', H-4'), 5.01 (1H, t, J=8.53 Hz, H-2'), 4.92 (1H, d, J=8.04 Hz, H-1'), 4.18–4.10 (4H, m, H-3, H-6a, H-6b, H-5'), 4.08 (1H, m, H-2), 3.75 (3H, s, COOCH$_3$), 3.60 (1H, m, H-5), 2.39 (2H, q, J=7.53 Hz, —CH$_2$CH$_3$), 2.11–2.01 (18H, m, Ac), 1.23 (3H, t, J=7.53 Hz, —CH$_2$CH$_3$)

EXAMPLE 12

Preparation of 2-ethyl-[1,2-di-deoxy-3-O-(sodium β-D-glucopyranosyluronate)-α-D-glucopyrano]-[2,1-d]-2-oxazoline In a two-necked flask, in an atmosphere of argon, 2-ethyl-[4,6-di-O-acetyl-1,2-di-deoxy-3-O-(methyl 2,3,4-tri-O-acetyl-β-D-glucopyranosyluronate)-α-D-glucopyrano]-[2,1-d]-2-oxazoline (54.0 mg, 0.0790 mmol) was dissolved in methanol (2.00 ml), and a methanol solution (108 μl, 0.0108 mmol) of sodium methoxide was added thereto at room temperature, followed by stirring for 1 hour for deblocking of the acetyl group. The solution was vacuum concentrated, and then dissolved in a 50 mM carbonic acid buffer solution (150 μl, pH 10.6), followed by stirring for 30 minutes to hydrolyze the methyl ester. The solution was vacuum concentrated to obtain colorless oily matter 2-ethyl-[1,2-di-deoxy-3-O-(sodium β-D-glucopyranosyluronate)-α-D-glucopyrano]-[2,1-d]-2-oxazoline.

Assignments of an NMR spectrum are as follows.
$^1$H NMR (400 MHz, D$_2$O): δ (ppm): 6.20 (1H, d, J=7.53 Hz, H-1), 4.75 (1H, d, J=8.03 Hz, H-1'), 4.40 (1H, m, H-2), 4.24 (1H, m, H-3), 3.96–3.83 (3H, m, H-4, H-6a, H-5'), 3.77 (1H, dd, J=6.02, 12.05 Hz, H-6b), 3.70–3.60 (2H, m, H-3', H-4'), 3.50–3.40 (2H, m, H-5, H-2'), 2.50 (2H, q, J=7.53 Hz, —CH$_2$CH$_3$), 1.26 (3H, t, J=7.53 Hz, —CH$_2$CH$_3$)

EXAMPLE 13

Preparation of 4,6-di-O-acetyl-2-deoxy-3-O-(methyl 2,3,4-tri-O-acetyl-β-D-glucopyranosyluronate)-2-(2-methylpropanamido)-D-glucopyranosyl acetate In a two-necked eggplant-type flask, benzyl 2-azido-2-deoxy-3-O-(methyl 2,3,4-tri-O-acetyl-β-D-glucopyranosyluronate)-β-D-glucopyranoside (107 mg, 0.175 mmol) was dissolved in methanol (6.00 ml), and 20% palladium hydroxide activated carbon (100 mg) was added thereto to carry out catalytic hydrogen reduction in an atmosphere of hydrogen for 24 hours to carry out deblocking of the benzyl group and conversion of the azide group into an amino group. After completion of the reaction, the insoluble matters were removed by filtration with celite, and the celite bed was washed with methanol (12.0 ml). Triethylamine (0.100 ml, 0.741 mmol) was added to the filtrate, and isobutylyl chloride (28.0 μl, 0.265 mmol) was added in a dry atmosphere at 0° C., followed by stirring at 0° C. for 3 hours. After completion of the reaction, pyridine (4.00 ml) was added thereto, and vacuum concentration was carried out to remove methanol, and acetic anhydride (3.00 ml, 31.5 mmol) was added thereto, followed by reaction at 0° C. for 1 hour and then at room temperature for 9 hours. After completion of the reaction, ice water was added tereto to decompose an excess amount of acetic anhydride, and then vacuum concentration was carried out. The residue was extracted with ethyl acetate and washed with 1M hydrochloric acid, a saturated sodium hydrogencarbonate aqueous solution and a saturated salt solution in this order for liquid separation. The organic layer was dried over anhydrous magnesium sulfate, insoluble matters were removed by filtration with celite and the filtrate was vacuum concentrated. The residue was purified by flash silica gel column chromatography (elution solvent: n-hexane/ethyl acetate=1/1–0/1) to obtain colorless oily matter 4,6-di-O-acetyl-2-deoxy-3-O-(methyl 2,3,4-tri-O-acetyl-β-D-glucopyranosyluronate)-2-(2-methylpropanamido)-D-glucopyranosyl acetate (53.0 mg, 0.0770 mmol, 44%, α/β=88/12).

The analysis data are as follows.
$^1$H NMR for α form (400 MHz, CDCl$_3$, TMS): δ (ppm): 6.05 (1H, d, J=3.52 Hz, H-1), 5.41 (1H, d, J=9.53 Hz, NH), 5.21–5.10 (2H, m, H-3', 4'), 5.06 (1H, dd, J=9.54, 10.04 Hz, H-4), 4.88 (1H, dd, J=7.53, 9.03 Hz, H-2'), 4.68 (1H, d, J=7.53 Hz, H-1'), 4.52 (1H, ddd, J=3.52, 9.53, 10.04 Hz, H-2), 4.19 (1H, dd, J=4.52, 12.55 Hz, H-6a), 4.08 (1H, dd, J=2.01, 12.55 Hz, H-6b), 4.03 (1H, d, J=9.04 Hz, H-5'), 3.96 (1H, dd, J=9.04, 10.04 Hz, H-3), 3.76 (1H, m, H-5), 3.75 (3H, s, COOCH$_3$), 2.38 (H, dq, J=6.53, 7.03 Hz, —CH(CH$_3$)$_2$), 2.20–2.00 (18H, m, Ac), 1.19 (3H, d, J=6.53 Hz, —CH(CH$_3$)$_2$), 1.15 (3H, d, J=7.03 Hz, —CH(CH$_3$)$_2$)

High Resolution FAB MS.
Calculated value: [M+H]$^+$=691.64 m/z (C$_{29}$H$_{41}$NO$_{18}$).
Measured value: 692 m/z.

EXAMPLE 14

Preparation of 2-(2-methylethyl)-[4,6-di-O-acetyl-1,2-di-deoxy-3-O-(methyl 2,3,4-tri-O-acetyl-β-D-glucopyranosyluronate)-α-D-glucopyrano]-[2,1-d]-oxazoline Employing a two-necked flask, in an atmosphere of argon, TMSOTf (23.0 μl, 0.125 mmol) was acted on 4,6-di-O-acetyl-2-deoxy-3-O-(methyl 2,3,4-tri-O-acetyl-β-D-glucopyranosyluronate)-2-(2-methylpropanamido)-D-glucopyranosyl acetate (51.2 mg, 0.0740 mmol) in 1,2-dichloroethane (3.00 ml) at 50° C. 3 hours later, completion of the reaction was confirmed, the reaction solution was cooled to 0° C., and triethylamine (40.0 μl, 0.296 mmol) was added thereto. Then, the reaction solution was vacuum concentrated, and the residue was purified by flash silica gel column chromatography (elution solvent: chloroform/methanol 40/1) and then by Sephadex LH-20 size exclusion chromatography to obtain colorless oily matter 2-(2-methylethyl)-[4,6-di-O-acetyl-1,2-di-deoxy-3-O-(methyl 2,3,4-tri-O-acetyl-β-D-glucopyranosyluronate)-α-D-glucopyrano]-[2,1-d]-oxazoline (26.4 mg, 0.0417 mmol, 56%).

Assignments of an NMR spectrum are as follows.

$^1$H NMR (400 MHz, CDCl$_3$, TMS): δ (ppm): 5.97 (1H, d, J=7.53 Hz, H-1), 5.30–5.18 (3H, m, H-4, H-3', H-4'), 5.01 (1H, dd, J=8.03, 9.03 Hz, H-2'), 4.92 (1H, d, J=8.03 Hz, H-1'), 4.20–4.08 (5H, m, H-2, H-3, H-6, H-5'), 3.75 (3H, s, COOCH$_3$), 3.59 (1H, m, H-5), 2.66 (1H, dq, J=6.53, 7.03 Hz, —CH(CH$_3$)$_2$), 2.10 (3H, s, Ac), 2.07 (3H, s, Ac), 2.04 (3H, s, Ac), 2.03 (3H, s, Ac), 2.02 (3H, s, Ac), 1.24 (3H, d, J=7.03 Hz, —CH(CH$_3$)$_2$), 1.23 (3H, d, J=6.53 Hz, —CH(CH$_3$)$_2$)

EXAMPLE 15

Preparation of 2-(2-methylethyl)-[1,2-di-deoxy-3-O-(sodium β-D-glucopyranosyluronate)-α-D-glucopyrano]-[2,1-d]-oxazoline In a two-necked flask, 2-(2-methylethyl)-[4,6-di-O-acetyl-1,2-di-deoxy-3-O-(methyl 2,3,4-tri-O-acetyl-β-D-glucopyranosyluronate) -α-D-glucopyrano]-[2,1-d]-oxazoline (26.4 mg, 0.0417 mmol) was dissolved in methanol (2.00 ml) in an atmosphere of argon, and a methanol solution (104 μl, 0.0104 mmol) of sodium methoxide was added thereto at room temperature, followed by stirring for 1 hour for deblocking of the acetyl group. The solution was vacuum concentrated, and then dissolved in a 50 mM carbonic acid buffer solution (300 μl, pH 10.6), followed by stirring for 1 hour to hydrolyze the methyl ester. The solution was vacuum concentrated to obtain colorless oily matter 2-(2-methylethyl)-[1,2-di-deoxy-3-O-(sodium β-D-glucopyranosyluronate)-α-D-glucopyrano]-[2,1-d]-oxazoline.

Assignments of an NMR spectrum are as follows.

$^1$H NMR (400 MHz, D$_2$O): δ (ppm): 6.20 (1H, d, J=7.53 Hz, H-1), 4.75 (1H, d, J=8.03 Hz, H-1'), 4.40 (1H, m, H-2), 4.24 (1H, m, H-3), 3.96–3.83 (3H, m, H-4, H-6, H-5'), 3.77 (1H, dd, J=6.02, 12.05 Hz, H-6), 3.70–3.60 (2H, m, H-3', H-4'), 3.50–3.40 (2H, m, H-5, H-2'), 2.50 (2H, q, J=7.53 Hz, —CH$_2$CH$_3$), 1.26 (3H, t, J=7.53 Hz, —CH$_2$CH$_3$)

EXAMPLE 16

Preparation of Hyaluronic Acid Derivative by Enzyme-catalyzed Polymerization

Of a solution having 2-ethyl-[1,2-di-deoxy-3-O-(sodium β-D-glucopyranosyluronate)-α-D-glucopyrano]-[2,1-d]-2-oxazoline obtained in Example 12 as a substrate monomer (hereinafter referred to as substrate monomer A, 18 mg, 0.044 mmol) dissolved in a heavy water carbonic acid buffer solution (300 μl), pH was adjusted to 7.1 by a DCl heavy water solution (1.0 M, 0.5 M, 0.1 M). 160 μl of the solution was put in each of NMR sample tubes (Entries 1 and 2). Heavy water (50.0 μl) and a solution having ovine testicular hyaluronidase (0.9 mg) (ICN Biomedicals Inc., Lot No. 9303B, 560 Units/mg) dissolved in heavy water (50.0 μl) were put in Entries 1 and 2, respectively, followed by well stirring, and variation with time at 30° C. was measured by $^1$H NMR. Methyl proton in the 2-position ethyl group of the oxazoline was taken as the internal standard, and the ratio of its integrated value to the integrated value of the reducing terminal 1-position proton of the oxazoline monomer was obtained to calculate the variation with time of the substrate monomer concentration. The results are shown in Table 5 and FIG. 6.

The same experiment was carried out by employing 2-(2-methylethyl)-[1,2-di-deoxy-3-O-(sodium β-D-glucopyranosyluronate)-α-D-glucopyrano]-[2,1-d]-oxazoline obtained in Example 15 as another substrate monomer (hereinafter referred to as substrate monomer B, 18 mg, 0042 mmol). The results are shown in Table 6.

TABLE 5

| | Residual ratio of substrate monomer A | |
|---|---|---|
| | Residual ratio (%) | |
| Time (hr) | No enzyme added (Entry 1) | Enzyme added (Entry 2) |
| 0.0 | 100 | 100 |
| 0.5 | 99.2 | 99.6 |
| 1.0 | 103 | 82.9 |
| 1.5 | 106 | 76.1 |
| 2.0 | 101 | 72.6 |
| 2.5 | 101 | 69.9 |
| 3.0 | 98.8 | 65.7 |
| 3.5 | 91.7 | 59.6 |
| 4.0 | 93.7 | 54.0 |
| 4.5 | 89.9 | 43.0 |
| 5.0 | 85.3 | 45.6 |
| 5.5 | 89.1 | 35.5 |
| 6.0 | 83.7 | 31.1 |
| 6.5 | 81.1 | 34.3 |
| 7.0 | 82.6 | 28.8 |
| 7.5 | 74.0 | 25.7 |
| 8.0 | 73.4 | 18.9 |
| 9.0 | 77.6 | 16.1 |
| 10.0 | 71.6 | 17.3 |
| 11.0 | 63.7 | 10.6 |
| 12.0 | 66.8 | 9.90 |
| 15.0 | 53.8 | 7.00 |
| 18.0 | 47.7 | 5.20 |
| 21.0 | 34.1 | 3.80 |
| 24.0 | 29.2 | — |
| 36.0 | 15.3 | — |
| 42.0 | 9.80 | — |

TABLE 6

Residual ratio of substrate monomer B

| Time (hr) | Residual ratio (%) | |
|---|---|---|
| | No enzyme added (Entry 1) | Enzyme added (Entry 2) |
| 0.0 | 100 | 100 |
| 0.5 | 98.0 | 93.8 |
| 1.0 | 90.2 | 93.0 |
| 1.5 | 88.6 | 87.7 |
| 2.0 | 84.9 | 81.9 |
| 2.5 | 86.2 | 88.5 |
| 3.0 | 83.4 | 85.9 |
| 3.5 | 79.7 | 83.8 |
| 4.0 | 78.0 | 81.5 |
| 4.5 | 79.2 | 74.8 |
| 5.0 | 76.0 | 78.9 |
| 5.5 | 75.9 | 76.8 |
| 6.0 | 70.9 | 73.3 |
| 6.5 | 70.8 | 73.3 |
| 7.0 | 67.6 | 72.0 |
| 7.5 | 68.4 | 67.8 |
| 8.0 | 66.1 | 66.8 |
| 9.0 | 60.7 | 62.6 |
| 10.0 | 57.2 | 55.7 |
| 11.0 | 53.1 | 53.3 |
| 12.0 | 49.8 | 50.1 |
| 15.0 | 41.5 | 35.4 |
| 18.0 | 33.7 | 27.1 |
| 24.0 | 19.9 | 11.8 |
| 36.0 | 4.5 | 5.5 |

Figure 6:
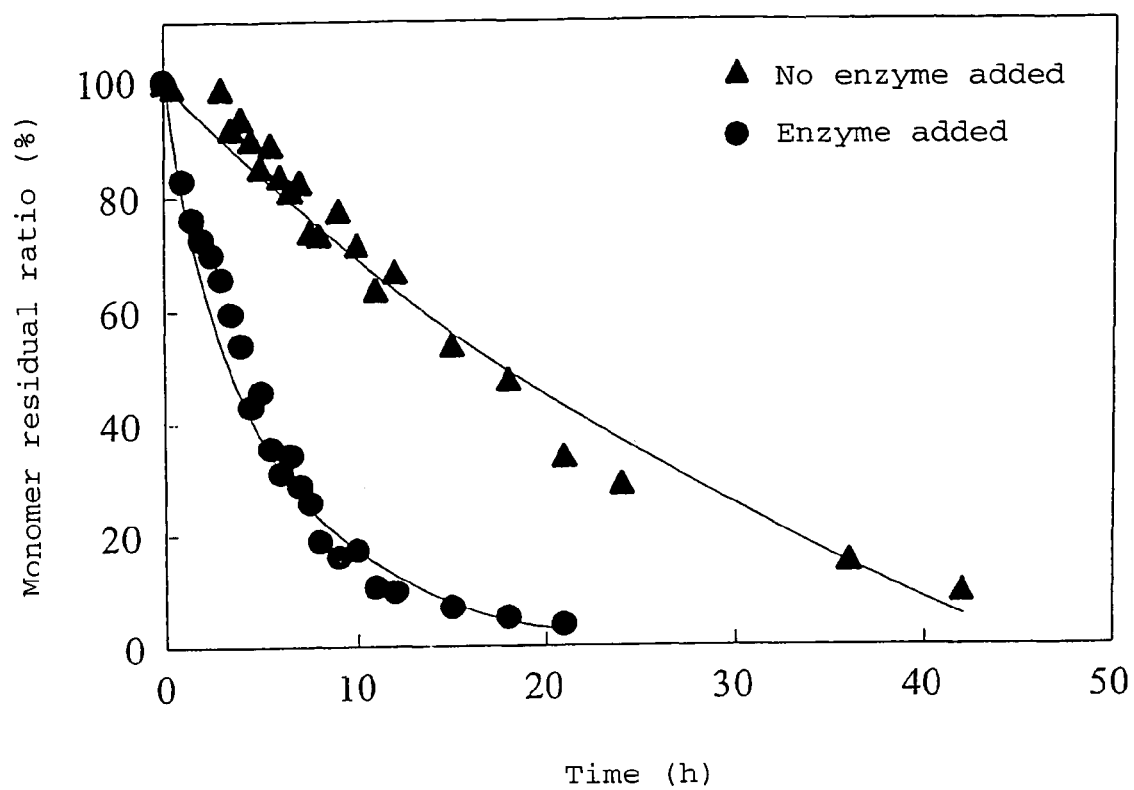
FIG. 6 illustrates a variation with time of a monomer substrate A in a reaction liquid.

As evident from the results shown in Table 5, FIG. 6 and Table 6, it becomes clear that consumption of the substrate monomers A and B is significantly accelerated in a system in which ovine testicular hyaluronidase is added as compared with a system in which no hyaluronidase is added, and it becomes clear that the substrate monomers A and B are recognized by the enzyme and ring-opening reaction of the oxazoline ring takes place.

In a system in which the hyaluronidase was added (Entry 2), after it was confirmed that the monomer consumption was completed, the polymer solution was soaked in a water bath of 90° C. for 3 minutes, whereby the enzyme was deactivated to terminate the reaction. The solution was subjected to GPC analysis, and the yield of the polymer product was obtained from the peak area. Then, purification by size exclusion chromatography (Sephadex™ G-10) was carried out, and the solvent after developing was freeze dried to obtain a product. The obtained product was analyzed by $^1$H NMR and GPC measurement. $^1$H NMR spectrum of a propanamide derivative obtained when the substrate monomer A was employed is shown in FIG. 7, and the results of GPC measurement of a propanamide derivative (product from the substrate monomer A) and a 2-methylpropanamide derivative (product from the substrate monomer B) are shown in Table 7. The GPC measurement was carried out employing the standard substance under the measurement conditions as disclosed in Example 6.

Assignments of an NMR spectrum are as follows.

$^1$H NMR (400 MHz, $D_2O$): δ (ppm): 4.59 (1H, d, J=7.03 Hz, H-1), 4.47 (1H, d, J=6.53 Hz, H-1'), 3.93–3.71 (6H, m, H-2, H-3, H-6, H-4', H-5'), 3.87 (1H, m, H-2), 3.57 (1H, m, H-3'), 3.53–3.50 (2H, m, H-4, H-5), 3.37 (1H, m, H-2'), 2.31 (2H, q, J=7.53 Hz, —$CH_2CH_3$), 1.12 (3H, t, J=7.53 Hz, —$CH_2CH_3$)

TABLE 7

Yield and molecular weight of formed hyaluronic acid derivatives

| Formed hyaluronic acid derivative (substrate monomer used) | Yield (%) | Mn | Mw | Mw/Mn |
|---|---|---|---|---|
| Propanamide derivative (substrate monomer A) | 66 | $8.02 \times 10^3$ | $1.10 \times 10^4$ | 1.37 |
| 2-Methylpropanamide derivative (substrate monomer B) | 20 | $1.65 \times 10^3$ | $1.84 \times 10^3$ | 1.11 |

INDUSTRIAL APPLICABILITY

The enzymatic method for producing hyaluronic acid or a hyaluronic acid derivative of the present invention is a simple preparation method as compared with a cockscomb extraction method or a fermentation method which has conventionally been employed industrially, and the present invention provides a method for producing hyaluronic acid or a hyaluronic acid derivative with which the product is easily isolated and purified from the reaction liquid. The obtained hyaluronic acid is industrially useful as a material for cosmetics, pharmaceutical products and biomedical materials.

The invention claimed is:

1. A method for producing hyaluronic acid or a hyaluronic acid derivative, which comprises:
reacting a hyaluronidase with an oxazoline derivative of the following formula (I):

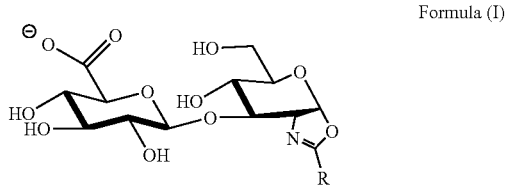

Formula (I)

wherein R is hydrogen, an alkyl group, an alkyl group which is optionally substituted, a phenyl group or a phenyl group which is optionally substituted.

2. The method according to claim 1, wherein the oxazoline derivative of formula (I) is 2-methyl-[1,2-dideoxy-3-O-(sodium-D-glucopyranosyluronate)]-α-D-glucopyrano-[2,1-d]-2-oxazoline.

3. The method according to claim 1, wherein the hyaluronidase is hyaluronidase from a mammal.

4. The method according to claim 3, wherein the hyaluronidase is bovine testicular hyaluronidase or ovine testicular hyaluronidase.

5. The method according to claim 1, wherein the hyaluronidase is reacted with 2-methyl-[1,2-dideoxy-3-O-(sodium -D-glucopyranosyluronate)]-α-D-glucopyrano-[2,1-d]-2-oxazoline at a pH ranging from 5 to 10.

6. The method according to claim 2, wherein the hyaluronidase is hyaluronidase from a mammals.

7. The method for producing hyaluronic acid or a hyaluronic acid derivative according to claim 2, wherein reacting is performed at a pH ranging from 5 to 10.

8. The method according to claim 3, wherein the hyaluronidase is reacted with 2-methyl-[1,2-dideoxy-3-O-(sodium -D-glucopyranosyluronate)]-α-glucopyrano-[2,1-d]-2-oxazoline at a pH ranging from 5 to 10.

9. The method for producing hyaluronic acid or a hyaluronic acid derivative according to claim 4, wherein the hyaluronidase is reacted with 2-methyl-[1,2-dideoxy-3-O-(sodium -D-glucopyranosyluronate)]-α-glucopyrano-[2,1-d]-2-oxazoline at a pH ranging from 5 to 10.

10. The method of claim 1, wherein R is hydrogen.

11. The method of claim 1, wherein R is an alkyl group.

12. The method of claim 1, wherein R is a substituted alkyl group.

13. The method of claim 1, wherein R is phenyl.

14. The method of claim 1, wherein R is substituted phenyl.

15. The method of claim 1, wherein said reacting occurs at a pH of from 6.5 to 9.5 and at a temperature of 20 to 40° C.

16. The method of claim 1, wherein the hyaluronidase is immobilized.

17. The method of claim 1, wherein reacting occurs in an aqueous solvent.

18. The method of claim 1, wherein reacting occurs in an aqueous solvent containing an alcohol or polyol.

19. The method of claim 1, wherein reacting occurs in an aqueous solvent containing an inorganic salt or a pH buffering agent which does not impair the reaction.

20. The method of claim 1, further comprising isolating and purifying the hyaluronic acid or hyaluronic acid derivative.

* * * * *